(12) United States Patent
Al-Omar

(10) Patent No.: US 10,449,300 B2
(45) Date of Patent: Oct. 22, 2019

(54) PLUNGER FOR SYRINGES AND SYRINGES

(71) Applicant: OMSI Sarl, Geneva (CH)

(72) Inventor: Hamad M. Al-Omar, Riyadh (SA)

(73) Assignee: OMSI Sarl, Geneva (CH)

( * ) Notice: Subject to any disclaimer, the term of this patent is extended or adjusted under 35 U.S.C. 154(b) by 0 days.

(21) Appl. No.: 15/546,897

(22) PCT Filed: Jan. 27, 2016

(86) PCT No.: PCT/EP2016/051678
§ 371 (c)(1),
(2) Date: Jul. 27, 2017

(87) PCT Pub. No.: WO2016/120312
PCT Pub. Date: Aug. 4, 2016

(65) Prior Publication Data
US 2018/0015227 A1     Jan. 18, 2018

(30) Foreign Application Priority Data

Jan. 27, 2015   (DE) .................... 10 2015 000 999

(51) Int. Cl.
*A61M 5/315*     (2006.01)
*A61M 5/178*     (2006.01)
*A61M 5/24*      (2006.01)

(52) U.S. Cl.
CPC .... *A61M 5/31568* (2013.01); *A61M 5/31515* (2013.01); *A61M 5/31595* (2013.01);
(Continued)

(58) Field of Classification Search
CPC .......... A61M 5/31568; A61M 5/31515; A61M 5/31595; A61M 5/178; A61M 5/31511;
(Continued)

(56) References Cited

U.S. PATENT DOCUMENTS 4,642,102 A * 2/1987 Ohmori ............. A61M 5/31555
                                                604/210
4,658,993 A * 4/1987 Vlasich .............. B65D 83/0027
                                                222/390

(Continued)

FOREIGN PATENT DOCUMENTS

| EP | 2 589 402 A1 | 5/2013 |
|---|---|---|
| WO | 2008/057976 A2 | 5/2008 |
| WO | 2010/132290 A2 | 11/2010 |

OTHER PUBLICATIONS

New Era Pump Systems Inc, 'NE-300 Just Infusion-™ Syringe Pump'. Apr. 24, 2012 [Database online] [Retrieved on Aug. 28, 2018] Retrieved from the Way Back Machine, https://web.archive.org/web/20120424171641/http://www.syringepump.com/download/NE-300Brochure.pdf.*

(Continued)

*Primary Examiner* — Nathan R Price
*Assistant Examiner* — Mark Alan Igel
(74) *Attorney, Agent, or Firm* — Eversheds Sutherland (US) LLP

(57) ABSTRACT

A plunger for a syringe may include a plunger head for fluid dense limiting a fluid chamber of the syringe, and a piston rod fixed to the plunger head. The piston rod may be formed by longitudinally extending axial webs that have an outwardly radial extension from the longitudinal axis and lead into a common crossing section. A free activation edge, which radially protrudes the radial extension may be provided on the piston rod and engageable with a vibration activator of a hollow body of the syringe to emit an acoustic signal. A swinging arm body may be arranged between two axial webs and couple the activation edge with the crossing section such that in case of a vibration activation in an axial direction the swinging arm body has a radial swinging arm (Continued)

Figure 1:
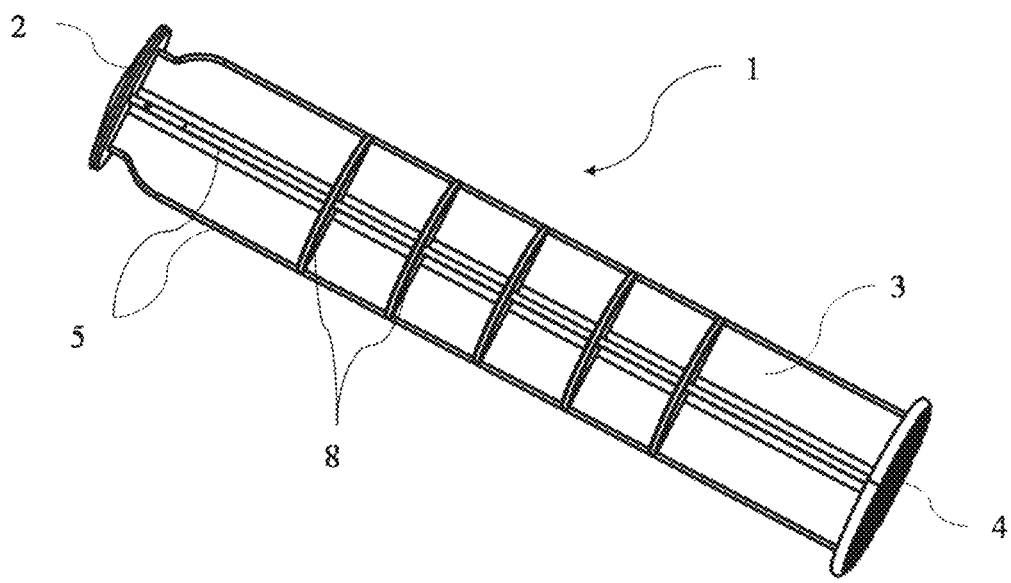

length between the activation edge and the crossing section of at least 40% of the radial extension.

19 Claims, 5 Drawing Sheets

(52) U.S. Cl.
CPC .............. *A61M 5/178* (2013.01); *A61M 5/24* (2013.01); *A61M 5/3158* (2013.01); *A61M 5/31511* (2013.01); *A61M 2005/31508* (2013.01); *A61M 2205/581* (2013.01); *A61M 2205/582* (2013.01)

(58) Field of Classification Search
CPC ........ A61M 5/315; A61M 2005/31523; A61M 2005/31508; A61M 2205/581; A61M 2205/582
See application file for complete search history.

(56) References Cited

U.S. PATENT DOCUMENTS

| | | | |
|---|---|---|---|
| 6,579,269 B1 * | 6/2003 | Kleyman | A61M 5/31555 604/207 |
| 8,394,068 B2 * | 3/2013 | Kosinski | A61M 5/31511 604/219 |
| D722,160 S * | 2/2015 | Armstrong | D24/130 |
| 9,457,153 B2 * | 10/2016 | Marano, Jr. | A61M 5/31568 |
| 9,770,559 B2 * | 9/2017 | Armstrong | A61M 5/31505 |
| 9,872,960 B2 * | 1/2018 | Tran | A61M 5/31595 |
| 2004/0186427 A1 * | 9/2004 | Pok | A61M 5/322 604/110 |
| 2006/0184136 A1 * | 8/2006 | Kleyman | A61M 5/31595 604/210 |
| 2008/0051728 A1 * | 2/2008 | Iijima | A61M 5/31511 604/221 |
| 2009/0287161 A1 * | 11/2009 | Traub | A61M 5/31595 604/208 |
| 2010/0076370 A1 * | 3/2010 | Howlett | A61M 5/1424 604/65 |
| 2011/0009829 A1 * | 1/2011 | Kosinski | A61M 5/31511 604/218 |
| 2011/0245780 A1 * | 10/2011 | Helmer | A61M 5/31515 604/211 |
| 2012/0184917 A1 * | 7/2012 | Bom | A61M 5/24 604/187 |
| 2013/0116628 A1 * | 5/2013 | Kulshrestha | A61M 5/31511 604/227 |
| 2015/0359969 A1 * | 12/2015 | Armstrong | A61M 5/31505 604/221 |
| 2016/0166772 A1 * | 6/2016 | Mirzazadeh | A61M 5/31526 604/222 |
| 2018/0015227 A1 * | 1/2018 | Al-Omar | A61M 5/31568 |

OTHER PUBLICATIONS

PCT International Search Report and Written Opinion for PCT Application No. PCT/EP2016/051678 dated Mar. 7, 2016 (14 pages).

* cited by examiner

1

PLUNGER FOR SYRINGES AND SYRINGES

CROSS REFERENCE TO RELATED APPLICATIONS

This application is a U.S. national stage application of PCT/EP2016/051678, filed Jan. 27, 2016, which claims priority to German Application No. 10 2015 000 999.0, filed Jan. 27, 2015. The contents of these applications are hereby incorporated by reference.

The present invention relates to a plunger for a syringe, particularly an injection syringe. Thereby the plunger is formed in a way that it provides a user with an acoustic and a haptic feedback in order to communicate the dispensed amount of fluid to the user when dispensing a predetermined amount of fluid. A conventional plunger for such a syringe comprises a plunger head for fluid dense limiting a fluid chamber of the syringe, which is limited from the outside by a particularly cylindrical hollow body. The liquid is pushed out of the fluid chamber through the plunger, which densely passes the hollow body to a dispensing end of the syringe, whereby it is important that a precise dispensing amount is predetermined.

Visual markings on the hollow body characterize different dispensing volumes, which correspond to certain amounts of fluid and therefore provide the user with a visual control over the dispensed amount of liquid. Such syringes have the disadvantage that the syringe has to be positioned in a visual field of the user. Further, this sort of dosing a desired amount of liquid presents a certain risk, because it can easily happen that too less or too much liquid is dispensed, even if an unrestricted view to the syringe is provided, because the position of the plunger, which corresponds to the marking, is frequently difficult to recognize because of the limited transparent material of the hollow body. Providing the user with an additional haptic feedback regarding the respective amount when dispensing the liquid overcomes this disadvantage. Hereto it is known to provide snapping or snatching elements extending radially and being arranged on the hollow body or on the plunger, which can snappingly be engaged with recesses or grooves. When inserting the plunger into the hollow body the elements of the plunger are in contact with the elements of the hollow body. This contact is tactile to the user through an increased or decreased resistance. Furthermore, it is known to enhance the haptic signal with an acoustic signal.

EP 2 289 393 A1 discloses a syringe with a hollow cylinder with markings on its outer surface, which correspond to different amounts of fluid. Additionally grooves are provided on the inner surface of the hollow cylinder at the axial height of the markings to which form the plunger head of the plunger is adapted in a way that when engaging with the grooves the plunger head snaps and provides the user with a haptic feedback. This functional integration at the plunger head has the disadvantage of a difficult and elaborate manufacturing of the plunger head and of the hollow cylinder and often leads to a dysfunction of the sealed plunger head, which particularly in the field of medicine technology is to avoid.

From WO 2005/058169 A2 a syringe with feedback elements is known which are arranged on the plunger as well as on the hollow cylinder to engage with one another and to provide acoustic and haptic signals. The feedback elements are formed as protrusions. When engaging a resistance has to be overcome at first, in order to provide an acoustic signal. The shaping of the protrusions as knobs or noses leads to an increase and decrease in resistance, so that a precise dosing is difficult. Further, the knob-form only provides a weak acoustic signal.

WO 2008/016381 A1 discloses a dosage device in form of a syringe pursuant to the subject-matter. The syringe provides pointed acoustic signal impulses, in order to communicate a predetermined dispensing dosage. Hereto, the piston rod of the plunger comprises several in series arranged encompassing ring-shaped protrusions, which are mounted on the axially passing edges of the axial webs, which build the piston rod. The ring-shaped protrusion has a radial extension, which is marginally bigger than an engaging element, which is arranged on an actuation flange of the hollow body. When inserting the plunger, the ring-shaped protrusion engages with the engaging element, whereby the acoustic signal is provided. A so designed syringe only provides a weak acoustic signal, too, which can be missed in case of usage.

It is therefore an object of the present invention to overcome the disadvantages of the known prior art, particularly providing a plunger for a syringe and a syringe with an enhanced haptic and acoustic feedback, particularly without effecting the functionality of the syringe and/or increasing the manufacturing costs.

This object is solved by the features of claim 1. Thereafter, a plunger for a syringe, particularly for an injection syringe is provided, which comprises a hollow body, which receives the plunger. The hollow body of the syringe defines a preferably cylindrical interior, whereby a hermetic sealing of the plunger is facilitated when dispensing the liquid. It is clear that other shapes of the interior of the hollow body can be provided as well. Particularly, according to the invention the plunger is designed to be upgradable for existing structures of the hollow body as long as the aspects according to the invention of the plunger are fulfilled. The plunger comprises a plunger head for fluid dense limiting a fluid chamber of the syringe, which is limited on one axial side by the plunger head through building a fluid dense slight bearing and particularly elsewhere exclusively by the hollow body, which comprises a dispensing opening at the end face opposite to the plunger head. Further, the plunger has a piston rod, which is fixed to the plunger head, with an actuation section, which particularly is disposed on the diametrically opposite side of the plunger head and which is suitable for actuating the plunger for inserting into the hollow body. The piston rod consists of several axially extending axial webs, which can be arranged point symmetrically to each other in the radial crossing section and particularly have a cross or a core shape. Depending on stability reasons at least three, particularly exactly three, four, six, eight axial webs can be provided in order to particularly set the stability of the structure of the piston rod. The number of the axial webs can also be used for increasing the number of acoustic feedback signals, and therefore reducing the dispensing volume, in order to dispense dosage units as precise as possible. The several axial webs are particularly arranged point symmetrically to the axial longitudinal axis of the piston rod. The axial webs comprise a radial extension, which measures from the axial longitudinal axis to an axial passing radial and edge of the respective axial web. The several axial webs radially inwardly extend from the axial passing radial end edge to the axial longitudinal axis of the piston rod and lead into a common core or crossing section, which particularly centrally receives the longitudinal axis. The piston rod further comprises at least one freely accessible activation edge, which radially protrudes over the radial extension of the several axial webs, and which when inserting the plunger, is engageable with a vibration activator, such that an acoustic signal is emitted. The acoustic signal is within an audible frequency range of at least 20 Hz, particularly at least 100 Hz or 500 Hz, particularly between 2,000 Hz and 5,000 Hz. In order to enhance the acoustic signal power, a swinging arm body is fixed between two axial webs on the piston rod. The swinging arm body builds particularly at this radial end the at least one free activation edge. According to the invention the swinging arm body structurally couples the at least one free activation edge directly with the core section of the piston rod providing that the swinging arm body and particularly thus also the at least one free activation edge comprise a radial swinging arm length between the activation edge and the crossing section of at least 40%, 50% or 60% of the radial extension in case of a vibration activation of the at least one free activation edge in an axial direction. The radial swinging arm length particularly results from considering the minimal radial distance of the engaging section of the activation edge to the axial longitudinal axis of the swinging arm length is measured from an external section of the core or crossing section of the axial webs to the radial external activation section of the activation edge. Preferably the radial swinging arm length of the swinging arm body is at least half the size of the mean radial extension. The at least one swinging arm body extends from its activation edge directly through forming material of the piston rod to the core section, so that this radially extending material bridge directly transfers the vibrations being initiated at the activation edge to the crossing section without necessarily having to transfer the vibrations through the axial webs, eventually being structurally coupled with the activation edge. This means that the activation edge can thoroughly be structurally coupled also with the adjacent axial webs. According to the invention a direct structural coupling between the activation edge and the core section is realized material binding through the swinging arm body.

The swinging arm body therefore extends, additionally to the axial webs, between the axial webs in a radial direction to the core section.

Should the axial webs consist of different radial extensions in certain embodiments of the piston rod the radial extension of the piston rod shall be determinable through a mean radial extension of the several axial webs. Along the swinging arm length between the activation edge and the crossing section the respective swinging arm body is particularly formed continuously out of full material, so that an activating vibration can be transferred in a directly radial direction to the crossing section. Preferably, the swinging arm body is formed as a swinging plate between the axial webs.

Preferably, the piston rod can be formed by four pairwise perpendicularly longitudinally extending axial webs. Thereby, the axial webs lead into a central crossing section, which receives the longitudinal axis, and limit in a circumferential direction pairwise each a swinging space with a triangular crossing section. The swinging space serves as a resonance chamber for enhancing the acoustic signal emitted by the swinging arm body in a way that two adjacent swinging arm bodies axially limit the swinging space in the longitudinal groove, which is limited by two axial webs. In a circumferential direction adjacent swinging spaces as well as in an axial direction adjacent swinging spaces can communicate which each other as longitudinal grooves on the axial webs and transition passages at the radial end of the swinging arm body can be formed. Preferably, the distance between two swinging arm bodies is bigger than the respective swinging arm length, preferably mean swinging arm length of the swinging arm body.

The basic shape of the swinging arm body can be formed differently regarding a plurality of swinging arm bodies. The basic shape of a swinging arm body can also consist of a pin or a stick shape, which is particularly cylindrical or has an angular crossing section. The stick or pin length extending from the crossing section corresponds to the swinging arm length. The absolute radial swinging arm length, which describes a second essential dimension of the ability of the swinging arm body to swing, arises from the difference of the radial distance of the respective activation edge to the longitudinal axis and the radial distance of the specific point on the crossing section to the longitudinal axis.

In a preferred embodiment of the invention the swinging arm body has a disc-shaped or a plate-shaped basic form, which extends particularly mainly in a circumferential and radial direction. A swinging arm body with a plate or a disc form is insofar advantageous, as a swinging space in an axial direction can be limited by the swinging arm body, whereby the resonance behavior when generating and transferring an acoustic signal is improved. Preferably, the especially disc- or plate-shaped swinging arm body can structurally merge into both adjacent axial webs except for a free axial edge of the axial webs and/or the swinging arm body can at least merge into one of the two axial webs except for the free accessible axial edge of the axial webs and/or the swinging arm body is not connected with any of the axial webs extending from the cross or core section. The plate-shaped swinging arm body is therefore preferably exclusively coupled with the crossing section, without affecting the ability of the swinging arm body to swing because of the axial webs.

In a preferred embodiment of the invention the plunger is produced from one piece together with the piston rod, the plunger head, and the swinging arm body, whereby walls of the axial webs and particularly disc-shaped walls of the swinging arm body having a substantially equal dimension.

Preferably, a plate-shaped swinging arm body comprises a substantially continuous wall thickness and/or is oriented with regard to the axial longitudinal axis of the piston rod such that said axis is perpendicular to the platewise extension of the swinging arm body. The axial webs as well, particularly in a longitudinal direction can be arranged perpendicular to the plate-shaped swinging arm body.

In an exemplary embodiment of the invention the swinging arm body has a plate-shaped form, which extends in a circumferentially direction around the longitudinal axis, whose thickness is smaller than substantially the twice, preferably is equal to the thickness of the plunger. Preferably, the thickness of the plate is in the area of the ideal wall thickness, which is between 0.7 to 1.3 times the thickness of the plunger. Preferably, the wall thickness is smaller than 2 mm, particularly between 0.5 to 1 mm.

In a further teaching of the invention the swinging arm body is produced from one piece together with the piston rod, particularly by injection molding with plastic, and/or built by several plate-sections that are arranged parallel to each other. Preferably, all components of the plunger are manufactured from one piece, particularly injection molded from one plastic piece.

In a preferred embodiment of the invention in every particularly funnel-shaped longitudinal groove of the piston rod, which is formed by two adjacent axial webs, swinging arm bodies that are preferably plate-shaped, particularly shaped in plate sections are arranged in series one behind another. The series of swinging arm bodies are preferably identically structured and extend having a plate-shaped basic form parallel to each other. The axial distances of the plates to each other are preferably identical but may also continuously get bigger or smaller according to a regulation of the dispensing volume.

Preferably, two in a circumferential direction adjacent rows of several swinging arm bodies are offset to each other in an axial direction, wherein the axial offset is continuously the same size. In a preferred embodiment of the invention the swinging arm bodies of two diametrically opposite rows are axially exactly opposite to each other, so that particularly oppositely arranged swinging arm bodies of a plate shaped swinging arm body are arranged on a common radial plane.

The plunger preferably comprises in axial direction a length in the range of at least 50 mm and 150 mm, particularly between 60 mm and 105 mm. A plunger head diameter is preferably between 5 mm and 30 mm, particularly between 9 mm and 20 mm. A swinging arm free end section of the plunger, which is related to the plunger head, extends in an axial direction preferably beyond 10 mm, particularly at least 15 mm, and less than 35 mm, particularly less than 30 mm. A swinging arm body free front section of the plunger heading the actuating section comprises an axial extension of preferably at least 15 mm and less than 35 mm, particularly at least 20 mm and less than 30 mm. The in circumferential direction adjacent rows of several swinging arm bodies comprise at least two, particularly five, particularly less than 15, swing arm bodies, which have an axial distance in the range from 5 mm to 25 mm, particularly 6 mm to 17 mm, to each other.

In a preferred embodiment of the invention the at least one activation edge extends in a circumferential direction particularly shaped in circular sections and/or over a sector angle $\alpha$ of less than 100°, preferably 95° or 90°, preferably between 5° and 90°, preferably between 10° and 60°. In an alternatively embodiment of the invention the axially defined activation edge can uninterruptedly completely circulate and thereby particularly describe a circular path. However, the activation edge can also comprise particularly radial inwardly displaced areas different to the circle path when having a continuous progression, so that only a certain section of the circulating activation edge can be engaged with the vibration activator of the hollow body. Particularly, a activation edge in sections can be advantageous for a circulating vibration activator at the hollow body.

It is clear that each activation edge or every pair of activation edges on the same axial height corresponds to an acoustic signal for a predetermined dispensing amount of the syringe.

In a further embodiment of the invention at least two activation edges are particularly structurally separated from each other arranged on the same axial position of the piston rod, wherein particularly the at least two activation edges having the same axial position are in sections substantially diametrically opposite to each other and/or are shaped in circular sections with the same circumferential extension. This supports a self-centering effect of the piston rod within the hollow body so that a plunger can be moved within the hollow body. The at least two activation edges are realized by two separate swinging arm bodies, in fact by its radial end sections, wherein particularly the two swinging arm bodies are structurally separated from each other, particularly separated from each other by axial webs.

In an exemplary embodiment of the invention the axial webs extend beyond adjacent areas of the swinging arm body, wherein particularly these step back areas have a smaller radial extension than the adjacent activation edge, in which the step back areas merge. Therefore, the step back areas do not serve as an activation edge and cannot be engagable with the vibration activator of the hollow body.

Further, the invention relates to a syringe, particularly to an injection syringe, particularly a medical injection syringe, which comprises a hollow body, and a plunger according to one of the preceding embodiments.

The hollow body particularly has a radial inwardly extending, preferably completely circumferential vibration activator, which for example is formed as a nose or a protrusion, which is positioned completely within the interior of the hollow body. Preferably, the vibration activator has a cone-shaped or funnel-shaped input area, whose inclination is less than 10° with regard to the longitudinal direction. The vibration activator can have a non-declined, particularly cylindrical sliding surface subsequent to the inclined activation chamber, wherein a profile jump, which is radially outwardly directed, follows the sliding surface, in order to obtain a free oscillation of the at least one activation edge.

In a further embodiment of the invention the swinging arm body of the piston rod and the vibration activator of the hollow body are designed with a radial oversize to each other, preferably between 0.05 to 2.0 mm. The radial oversize particularly depends on the dimensions of the syringe itself. Syringes with big radial dimensions have an oversize between 0.5 to 2.0 mm, while narrower syringes have an oversize of less than 0.5 mm, particularly less than 0.1 mm. In an advantageous embodiment the inner diameter of the oscillation of the hollow body can be 15.55±0.05 mm and the outer diameter of the vibration activator of the plunger can be 15.70±0.05 mm. Thus, the swinging arm body is excited to oscillate by the activation edge, in order to emit an acoustic signal.

In a further embodiment of the invention an axial length of the vibration activator of the hollow body is aligned with the axial distance of two axial adjacent swinging arm bodies such, that the two adjacent swinging arm bodies are in engagement with the vibration activator. This has the advantage of a good guiding of the plunger within the hollow body and a tilting of the plunger head can be avoided.

Figure 2:
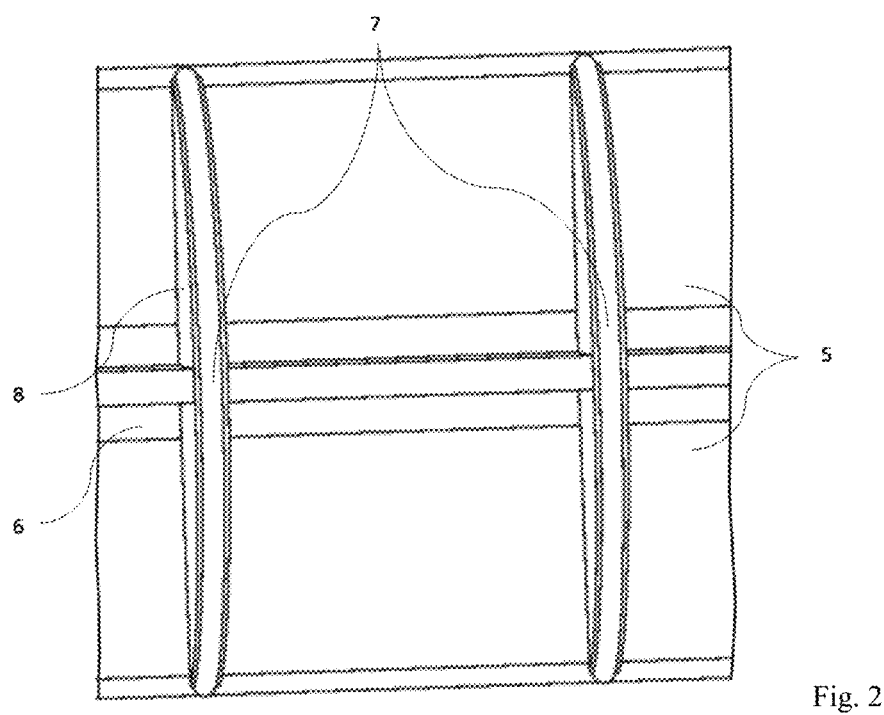
Figure 3:
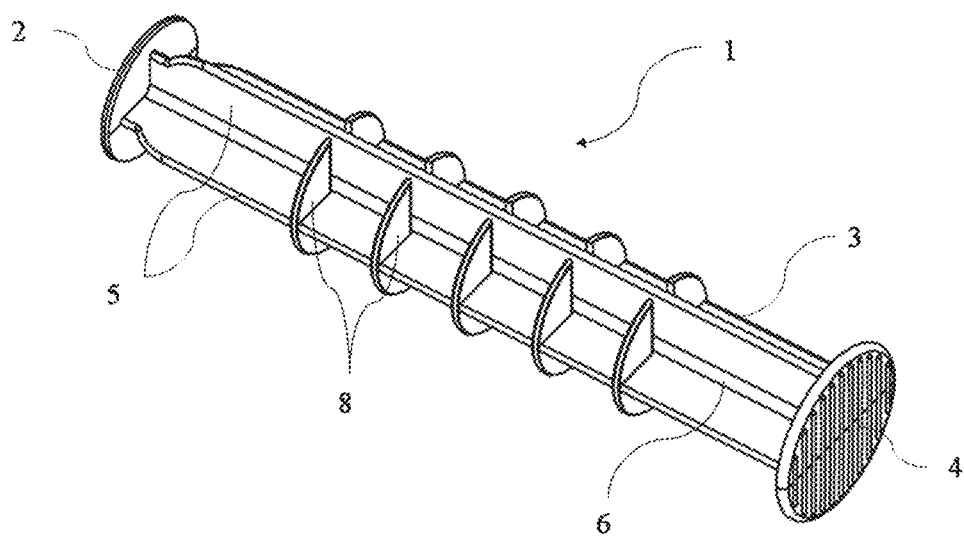
Figure 4:
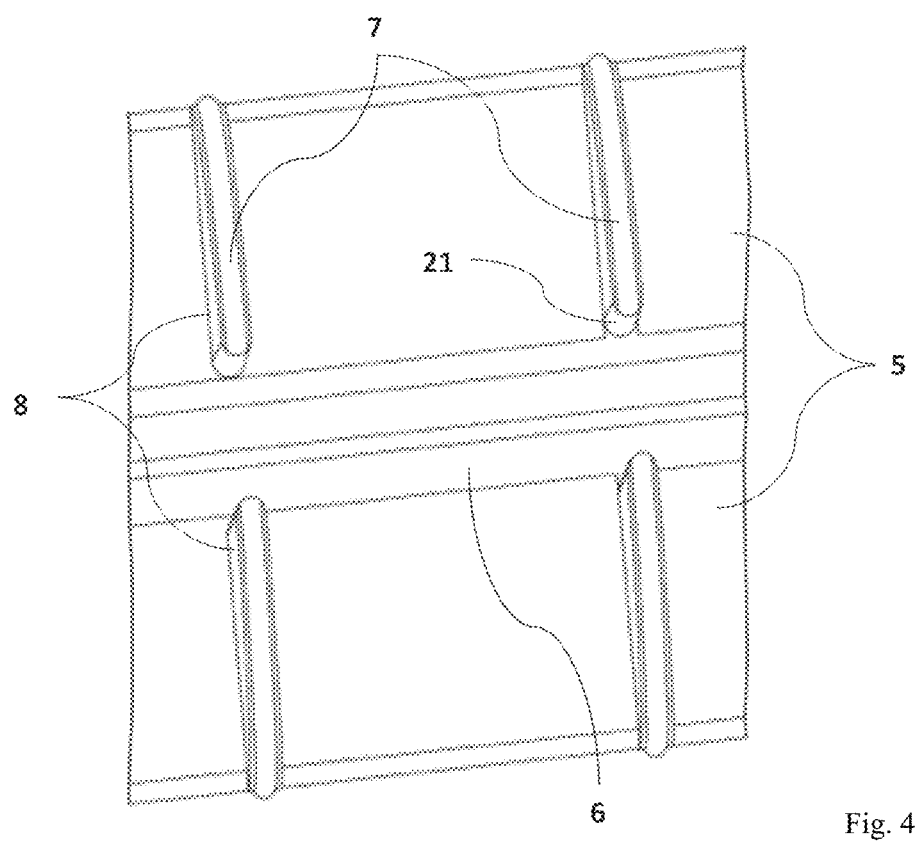
Figure 5:
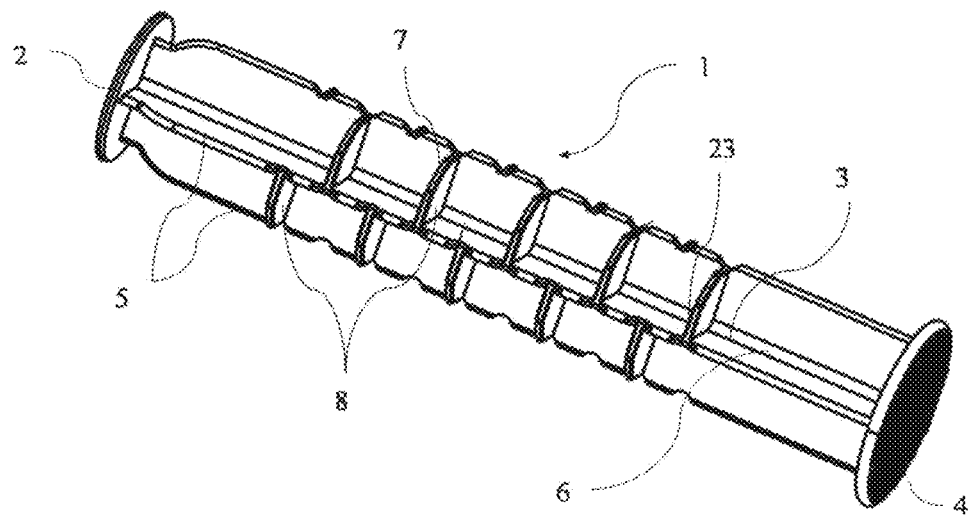
Figure 6:
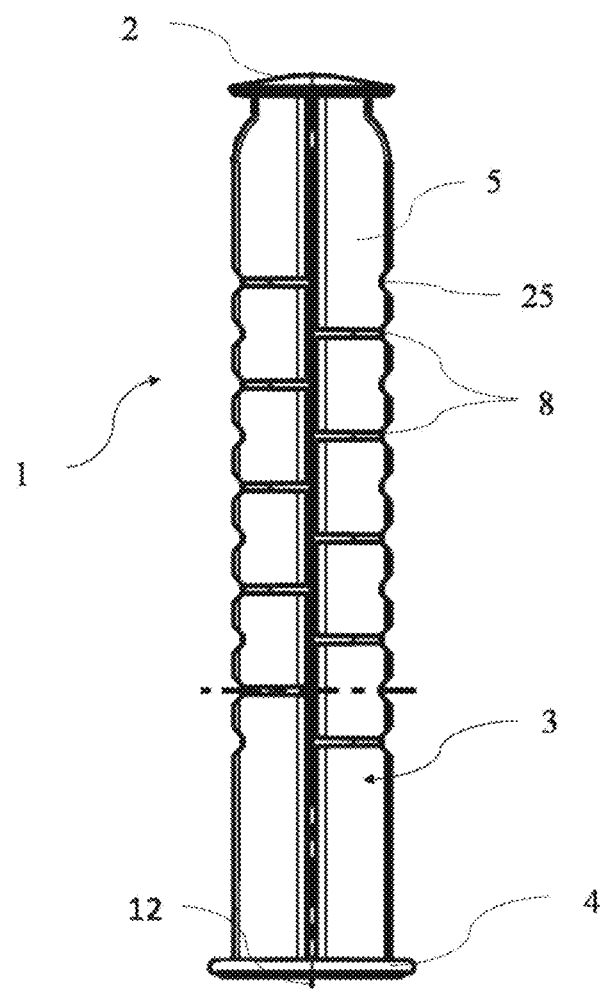
Figure 7:
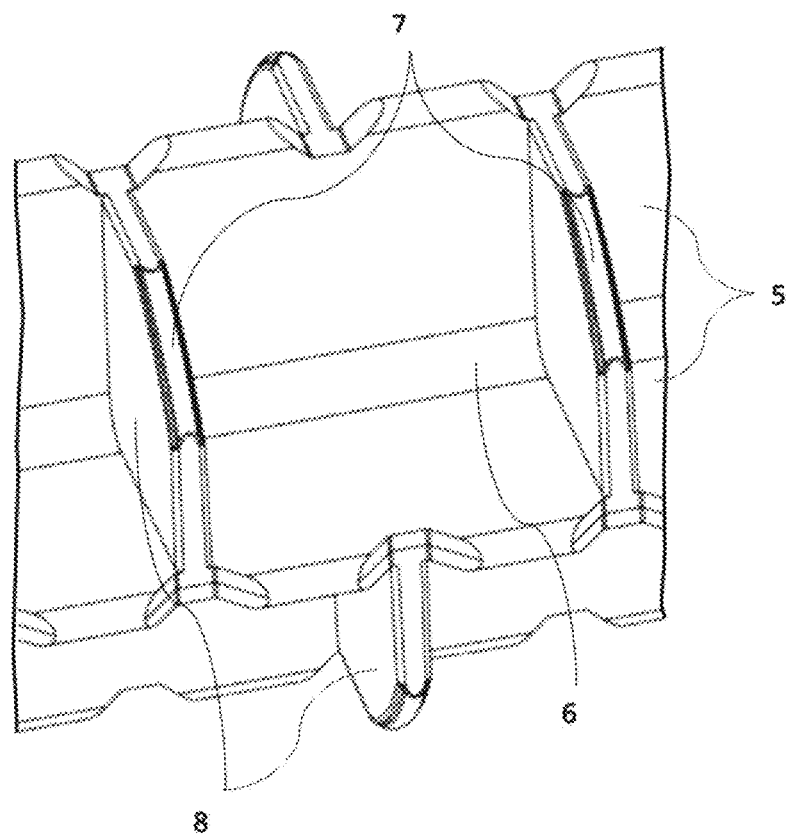
Figure 8:
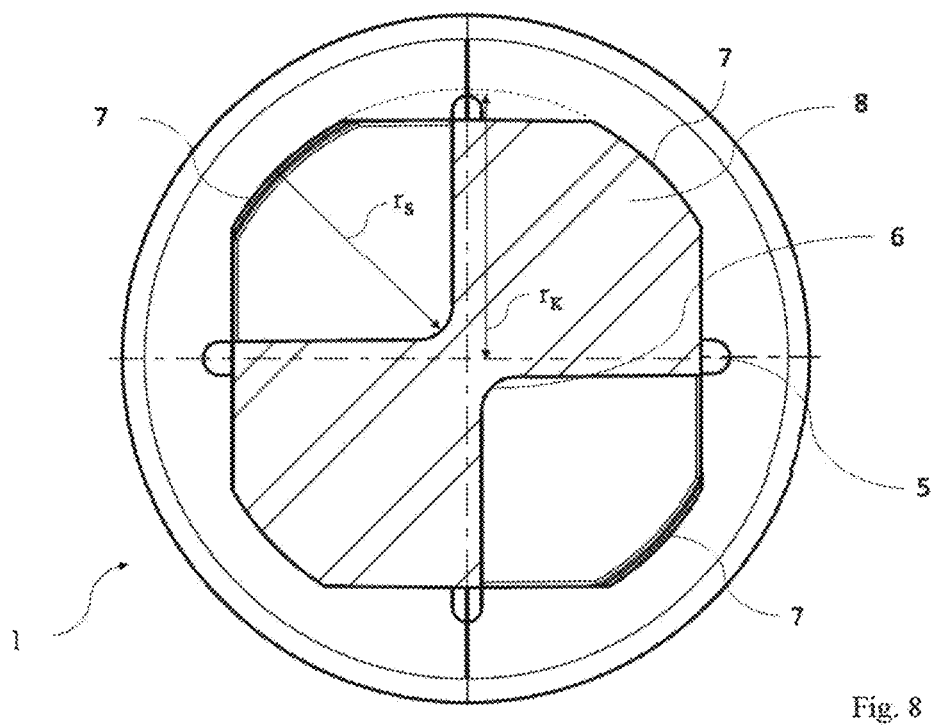
Figure 9:
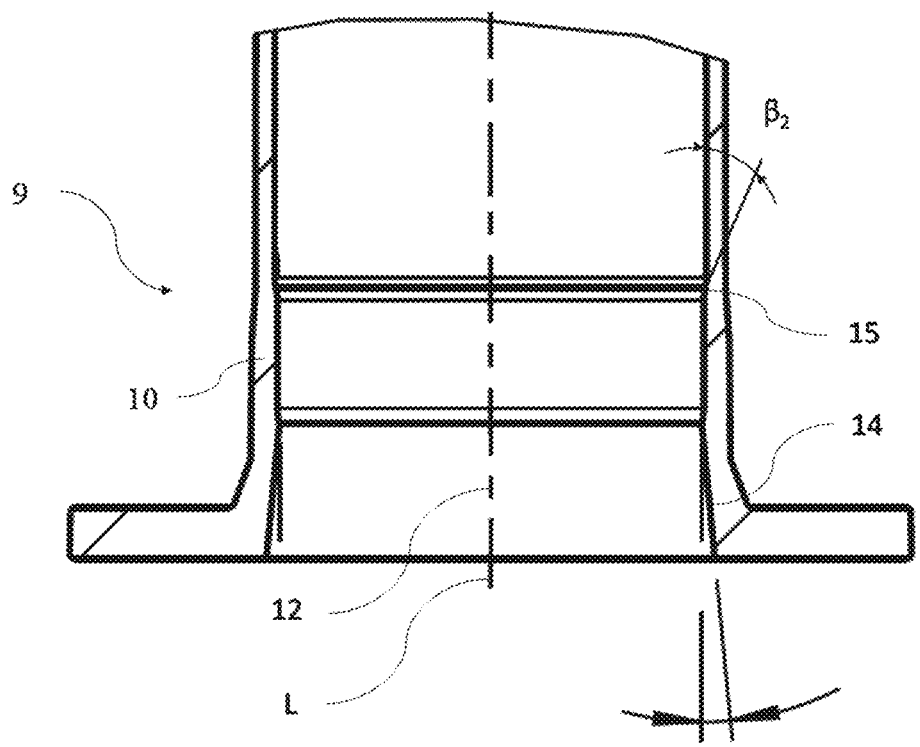

In the following further features, characteristics and advantages of the present invention will become more readily apparent in view of the following detailed description of the currently preferred embodiments and accompanying drawings, which show:

FIG. 1 a perspective view of a first embodiment of the plunger according to the invention;

FIG. 2 a perspective view of an enlarged section of a piston rod of the plunger according to FIG. 1;

FIG. 3 a perspective view of a second embodiment of the plunger according to the invention;

FIG. 4 a perspective view of an enlarged section of the piston rod of the plunger according to FIG. 3;

FIG. 5 a perspective view of a third embodiment of the piston rod of the plunger;

FIG. 6 shows a side view of the plunger according to FIG. 5;

FIG. 7 a perspective view of an enlarged section of four swinging arm bodies of the plunger according to FIGS. 5 and 6;

FIG. 8 a cross sectional view of the third embodiment of the plunger according to the invention;

FIG. 9 an enlarged section of a hollow body; and

Figure 10:
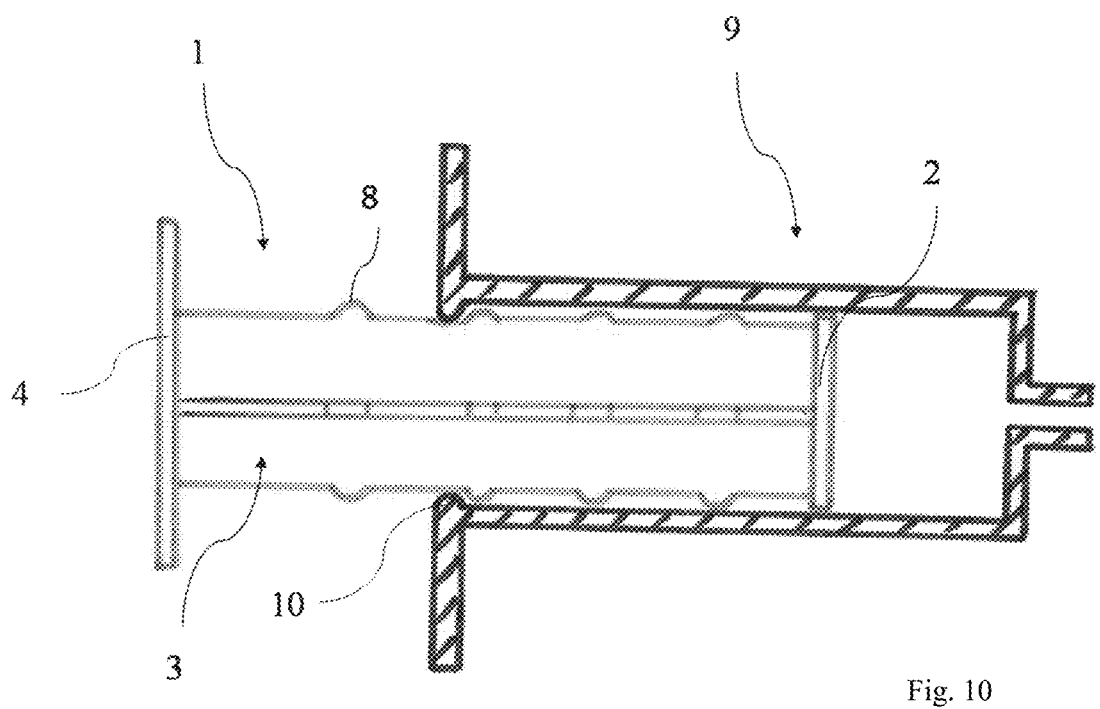

FIG. 10 a schematic illustration of the functionality of the invention.

FIGS. 1 and 2 relate to a first embodiment of the plunger 1. The plunger 1 thus comprises a piston rod 3, at whose one end a plunger head 2 and at whose other end an activation section 4 is positioned. The piston rod 3 is built by four pairwise perpendicular axial webs 5. The axial webs 5 merge into a common central cross or core section 6, which receives the longitudinal axis. FIG. 2 shows an enlarged view of two of the parallel on the piston rod 3 arranged circumferentially extending swinging arm bodies 8. The swinging arm bodies 8 comprise of a completely circumferentially disc- or plate-shaped basic form and also a completely circumferential activation edge 7, at whose radial outwardly pointing edge. The radial distance of the swinging arm bodies 8 to the longitudinal axis 12 is thus bigger than the radial distance of the axial webs 5 to the longitudinal axis 12 of the plunger 1.

In FIG. 1 several, particularly more than three swinging arm bodies, preferably in this example five swinging arm bodies are arranged parallel to each other having a certain distance to adjacent swinging arm bodies 8 on the piston rod 3, which limit five resonance chambers within the hollow body 9 of the syringe.

Two perpendicular to each other arranged axial webs 5, and adjacent to each other, form a longitudinal groove of the piston rod 3. At the bottom of the longitudinal groove, thus at the deepest position regarding a radial direction, the transition area between the two axial webs 5 is rounded. As can be seen in FIG. 8, a swinging arm length $r_S$ is defined as a radial distance of the free activation edge 7. Further, it can be seen that the actuation section 4, which is fixed parallel to the swinging arm bodies 8 of the piston rod 3, comprises a bigger radial distance to the longitudinal axis 12 of the piston rod. In FIGS. 1 and 2 a small radial oversize of the activation edge 7 with regard to the longitudinal edge of the axial webs 5 is not further indicated, however, it is clear that the vibration activator 10 of the hollow body 2 is measured relative to the radial dimensions of the axial webs and the swinging arm bodies 8, respectively the activation edge 7 such that a snapping engagement is exclusively built between the vibration activator 10 and the respective activation edge 7.

When inserting the plunger 1 according to the invention into an exemplary in FIGS. 9 or 10 illustrated hollow body, which, however, can also be formed as a conventional hollow body with an inwardly extending activation nose, the swinging arm bodies 8 engage with the activation nose and are activated to oscillate in an axial direction, whereby an audible sound is realized through vibration activation of the plate-shaped swinging arm body 8.

The distance between two adjacent disc-shaped swinging arm bodies 8 defines the volume unit, whose complete dispension produces an acoustic signal. Naturally, the predetermined amount of fluid, for which an acoustic signal should be emitted, can be set through reducing the axial distance between two disc-shaped swinging arm bodies.

In FIGS. 3 and 4 perspective views of the second embodiment of the invention are shown. For a better readability of the description of the figures the same reference signs as in the embodiment according to FIGS. 1 and 2 are used for similar or identical components of the plunger according to the invention. According to FIGS. 3 and 4 the plunger 1 differs from the embodiment according to FIGS. 1 and 2 such that the swinging arm body is contactless with regard to one of the adjacent axial webs 5. One axial web is separated from the swinging arm body through a gap. On each half of the piston rod a pair of swinging arm bodies 8 is arranged, wherein each swinging arm body substantially builds a quarter disc.

At each predetermined axial position a pair of substantially identical, in a circumferential orientation of substantially 180° extending, plate- or disc-shaped swinging arm bodies 8 are arranged on the piston rod. The swinging arm bodies 8 are fixed to the plunger 1 such that two first opposite axial webs 5 are connected with the swinging arm bodies and two second opposite axial webs each have a distance to the swinging arm bodies 8, so that a free space 21 between the second axial webs 5 and the swinging arm bodies 8 in a radial direction is formed.

FIGS. 5 to 8 relate to a third embodiment of the plunger 1 according to the invention. For an easy readability of the description of the figures the same reference signs shall be used for identical or similar components of the plunger 1. The piston rod 3 forms at one axial position two structurally in a circumferential direction separated activation edges 7, which are arranged separately diametrically opposite to each other and comprise the same circumferential extension.

As can be seen in FIGS. 5 and 6, two in a circumferential direction adjacent swinging arm bodies 8 are arranged axially offset to each other. The axial offset is substantially equal to half of the distance between two in an axial direction adjacent swinging arm bodies 8, which are disposed in a row within the longitudinal groove of the piston rod 3. Thus, the number of acoustic signals can be doubled and the dosing amount for each acoustic signal is reduced.

It is clear that through a reproduction of the longitudinal grooves by more than four axial webs 5 a further potential of increasing the acoustic signals regarding one push stroke of the plunger 1 can be achieved. The swinging arm body comprises both of a disc sector form and a sectorwise activation edge 7, whose circumferential extension is less than 45°. In FIG. 8 the sectorwise form of the activation edge 7 of the swinging arm bodies 8 can be seen. Here, the swinging arm body 8 comprises a circumferentially over the sector angle α extending activation edge 7, and in the further progression two substantially straight setback edges 23, which are not in engagement with the vibration activator 10 of the hollow body 9. The setback edges 23 pass perpendicular to the axial longitudinal direction L and lead into a recess 25, which is incorporated into the axial edge of the axial webs 5, in order to enable a transmission of signal oscillations between each of the resonance chambers limited by the swinging arm bodies 8.

In FIG. 8 the radial distance of the axial webs 5 to the longitudinal axis 12 of the plunger respective the plunger radius $r_K$ is shown. Further, the swinging arm length $r_S$, which radially inwardly extends from the activation edge 7 to the core section 6, particularly to the rounded bottom of the axial groove 5, is clearly bigger than the half of the mean radial extension $r_K$, whereby a clear reinforcement of the acoustic power of the swinging arm body 8 is realized.

In FIG. 9 a geometric embodiment of the vibration activator 10 of the hollow body 9 of the syringe according to the invention is shown. The radial circumferential vibration activator 10 is arranged on the inner surface of the hollow body 9 and comprises a lead-in input area 14 with a phase angle $\beta_1$ and a lead-out profile step 15 with a phase angle $\beta_2$, wherein $\beta_1$ is clearly smaller than $\beta_2$. The phase angle $\beta_1$ is preferably under 20°, wherein the phase angle $\beta_2$ is bigger than 25°.

In FIG. 10 a schematic diagram is shown to clarify the functionality of the invention. The plunger 1 is hereby inserted into an opening of the hollow body 9, in order to dispense fluid, which is located in the interior of the hollow body 9. It can be seen that between the swinging arm bodies 8, arranged on the piston rod 2, and the vibration activator 10 of the hollow body 9 an oversize is built. Thus, firstly, an increased resistance has to be overcome when inserting, until at the end of the engagement process between one swinging arm body 8 and the vibration activator 10 the swinging arm body 8 slides from the vibration activator 10, wherein the resistance quickly reduces and the swinging arm body 8 emits an acoustic signal, particularly a click noise, through compensating the elastic deformation of the swinging arm body 8 during the engagement process. The swinging arm body 8 (swinging plate), which radially continuously interruption-free, without a gateway or an opening, extends from the core section 6 maintains an extended swinging arm length $r_s$ according to the invention, whereby the oscillation signal is clearly increased when activated through an vibration activator. The swinging arm length $r_S$ regarding a radial direction is, without considering the axial webs, clearly enlarged with regard to the prior art.

The features disclosed in the above description, the figures and the claims may be significant for the realisation of the invention in its different embodiments individually as in any combination.

The invention claimed is:

1. A plunger for a syringe having a hollow body for receiving the plunger, the plunger comprising a plunger head for sealing a fluid chamber of the syringe, and a piston rod fixed to the plunger head with an actuation section, at which the plunger can be actuated for inserting into the hollow body, wherein the piston rod is formed by axial webs extending along a longitudinal axis of the plunger, the axial webs having an outwardly radial extension from the longitudinal axis and leading into a common crossing section along the longitudinal axis, wherein a first free activation edge is provided on the piston rod and radially protrudes from the radial extension, wherein the first free activation edge is engageable with a vibration activator of the hollow body such that an acoustic signal is emitted when the plunger is inserted into the hollow body, wherein a first swinging arm body is arranged circumferentially between a first axial web and a second axial web of the axial webs and couples the first free activation edge with the crossing section, wherein the first swinging arm body is contactless with the second axial web forming a free space between the second axial web and the first swinging arm body, and wherein the first swinging arm body has a radial swinging arm length between the first free activation edge and the crossing section of at least 40% of the radial extension.

2. The plunger according to claim 1, wherein the first swinging arm body has a disc- or plate-shaped form and extends in a circumferential direction with respect to the longitudinal axis.

3. The plunger according to claim 1, wherein the first swinging arm body has a wall thickness that is smaller than two times a wall thickness of the axial webs.

4. The plunger according to claim 1, wherein the first swinging arm body is integrally formed with the piston rod by injection molding with plastic.

5. The plunger according to claim 1, wherein the first free activation edge extends in a circumferential direction with respect to the longitudinal axis along a sector angle of less than 100°.

6. The plunger according to claim 1, wherein the first free activation edge and a second free activation edge are separately arranged at a common axial position along the piston rod, and wherein the first free activation edge and the second free activation edge are arranged opposite one another in a circumferential direction with respect to the longitudinal axis.

7. The plunger according to claim 2, wherein the first axial web and the second axial web radially protrude from the first swinging arm body.

8. A medical injection syringe, comprising the hollow body and the plunger according to claim 1.

9. The plunger according to claim 1, wherein a radial overlap exists between the first swinging arm body and the vibration activator so that the first swinging arm body radially engaged the vibration activator when the plunger is axially moved into the hollow body.

10. The plunger according to claim 9, wherein a second swinging arm body is provided on the piston rod and spaced apart from the first swinging arm body by an axial distance along the longitudinal axis, and wherein an axial length of the vibration activator is equal to or greater than the axial distance.

11. The plunger according to claim 10, wherein a third swinging arm body and a fourth swinging arm body are provided on the piston rod and spaced apart from one another by the axial distance along the longitudinal axis, wherein the third swinging arm body and the fourth swinging arm body are offset from the first swinging arm body and the second swinging arm body in a circumferential direction with respect to the longitudinal axis, wherein the third swinging arm body is spaced apart from the first swinging arm body by approximately half the axial distance along the longitudinal axis, and wherein the fourth swinging arm body is spaced apart from the second swinging arm body by approximately half the axial distance along the longitudinal axis.

12. The plunger according to claim 1, wherein the first swinging arm body has a wall thickness that is smaller than a wall thickness of the axial webs.

13. The plunger according to claim 1, wherein the first free activation edge extends in a circumferential direction with respect to the longitudinal axis along a sector angle of less than 90°.

14. The plunger according to claim 1, wherein the first free activation edge extends in a circumferential direction with respect to the longitudinal axis along a sector angle of between 5° and 90°.

15. The plunger according to claim 1, wherein the first free activation edge extends in a circumferential direction with respect to the longitudinal axis along a sector angle of between 10° and 60°.

16. The plunger according to claim 9, wherein the radial overlap is between 0.05 to 0.5 mm.

17. The plunger according to claim 1, wherein the first swinging arm body is connected to the first axial web.

18. The plunger according to claim 1, wherein the first swinging arm body is contactless with the first axial web forming a second free space between the first axial web and the swinging arm body.

19. A plunger for a syringe having a hollow body for receiving the plunger, the plunger comprising a plunger head for sealing a fluid chamber of the syringe, and a piston rod fixed to the plunger head with an actuation section, at which the plunger can be actuated for inserting into the hollow body, wherein the piston rod is formed by axial webs extending along a longitudinal axis of the plunger, the axial webs having an outwardly radial extension from the longitudinal axis and leading into a common crossing section along the longitudinal axis, wherein a first free activation edge is provided on the piston rod and radially protrudes from the radial extension, wherein the first free activation edge is engageable with a vibration activator of the hollow body such that an acoustic signal is emitted when the plunger is inserted into the hollow body, wherein a first swinging arm body is arranged circumferentially between a first axial web and a second axial web of the axial webs and couples the first free activation edge with the crossing section, and wherein the first swinging arm body is contactless with the second axial web forming a free space between the second axial web and the first swinging arm body.

* * * * *